(12) United States Patent
Kang et al.

(10) Patent No.: US 11,998,543 B2
(45) Date of Patent: Jun. 4, 2024

(54) PHARMACEUTICAL COMPOSITION COMPRISING ALDEHYDE INHIBITOR AND ANTICANCER AGENT FOR TREATMENT OF BRAIN CANCER

(71) Applicants: Industry-Academic Cooperation Foundation, Yonsei University, Seoul (KR); National Cancer Center, Goyang-si (KR)

(72) Inventors: Seok-Gu Kang, Suwon-si (KR); Soo Youl Kim, Goyang-si (KR)

(73) Assignees: Industry-Academic Cooperation Foundation, Yonsei University, Seoul (KR); National Cancer Center, Goyang-si (KR)

( * ) Notice: Subject to any disclaimer, the term of this patent is extended or adjusted under 35 U.S.C. 154(b) by 716 days.

(21) Appl. No.: 17/259,029

(22) PCT Filed: May 17, 2019

(86) PCT No.: PCT/KR2019/005906
§ 371 (c)(1),
(2) Date: Jan. 8, 2021

(87) PCT Pub. No.: WO2020/013434
PCT Pub. Date: Jan. 16, 2020

(65) Prior Publication Data
US 2021/0267969 A1     Sep. 2, 2021

(30) Foreign Application Priority Data
Jul. 9, 2018 (KR) .................. 10-2018-0079157

(51) Int. Cl.
| | |
|---|---|
| A61K 31/495 | (2006.01) |
| A61K 31/11 | (2006.01) |
| A61K 31/155 | (2006.01) |
| A61K 45/06 | (2006.01) |
| A61P 35/04 | (2006.01) |

(52) U.S. Cl.
CPC ............ *A61K 31/495* (2013.01); *A61K 31/11* (2013.01); *A61K 31/155* (2013.01); *A61K 45/06* (2013.01); *A61P 35/04* (2018.01)

(58) Field of Classification Search
CPC .... A61K 31/495; A61K 31/11; A61K 31/155; A61K 45/06; A61P 35/04
USPC ........................................................ 514/393
See application file for complete search history.

(56) References Cited

U.S. PATENT DOCUMENTS

| | | | |
|---|---|---|---|
| 6,114,397 | A | 9/2000 | Flack et al. |
| 2009/0010878 | A1 | 1/2009 | Holmlund et al. |
| 2017/0071877 | A1 | 3/2017 | Kim et al. |
| 2019/0254995 | A1 | 8/2019 | Kang et al. |
| 2019/0388366 | A1 | 12/2019 | Cheong et al. |
| 2021/0290570 | A1* | 9/2021 | Kim ........................ A61P 35/00 |

FOREIGN PATENT DOCUMENTS

| | | |
|---|---|---|
| KR | 10-2015-0102152 A | 9/2015 |
| KR | 10-2016-0094861 A | 8/2016 |
| KR | 10-2018-0045884 A | 5/2018 |

OTHER PUBLICATIONS

Park et al., "Regulation of bioenergetics through dual inhibition of aldehyde dehydrogenase and mitochondrial complex I suppresses glioblastoma tumorspheres", Neuro-Oncology, 2018, 20(7), 954-965.
Valtorta et al., "Metformin and temozolomide, a synergic option to overcome resistance in glioblastoma multiforme models", Oncotarget, 2017, 8(68), 113090-113104.
Stupp et al., "Radiotherapy plus Concomitant and Adjuvant Temozolomide for Glioblastoma", The New England Journal of Medicine, 2005, 352(10), 987-996.
International Search Report dated Aug. 30, 2019, in connection with International Application No. PCT/KR2019/005906, 7 pages.
Written Opinion dated Aug. 30, 2019, in connection with International Application No. PCT/KR2019/005906, 5 pages.

* cited by examiner

*Primary Examiner* — Kristin A Vajda
(74) *Attorney, Agent, or Firm* — McDonnell Boehnen Hulbert & Berghoff LLP

(57) ABSTRACT

The present disclosure relates to a pharmaceutical composition for treating brain cancer containing an aldehyde inhibitor and an anticancer drug. Since there are many types of brain cancer and the boundary between brain cells and tumor cells in brain cancer is not clear, brain cancer is particularly difficult to treat. The pharmaceutical composition of the present disclosure may further contain a biguanide-based compound as needed, wherein the compound is preferably phenformin. The pharmaceutical composition of the present disclosure is very effective for the treatment and improvement of prognosis of brain cancer, and has remarkable effects of killing cancer cells and inhibiting cancer stem cell characteristics, compared to when each of the active ingredients is administered alone. Thus, it is expected that the pharmaceutical composition of the present disclosure will be widely used in the field of brain cancer treatment.

20 Claims, 8 Drawing Sheets

PHARMACEUTICAL COMPOSITION COMPRISING ALDEHYDE INHIBITOR AND ANTICANCER AGENT FOR TREATMENT OF BRAIN CANCER

CROSS-REFERENCE TO RELATED APPLICATIONS

This application is a U.S. National Stage entry of International Patent Application no. PCT/KR2019/005906, filed May 17, 2019, which claims the benefit of priority of Korean Patent Application no. 10-2018-0079157, filed Jul. 9, 2018.

TECHNICAL FIELD

The present disclosure relates to a pharmaceutical composition for treating brain cancer containing an aldehyde inhibitor and an anticancer drug.

BACKGROUND ART

Cancer is one of the most common causes of death worldwide. Approximately 10 million new cancer cases occur each year, and cancer accounts for approximately 12% of all death causes, which is the third leading cause of death. Accordingly, efforts have been made to develop effective anticancer drugs, and a number of anticancer drugs have been developed that more effectively kill cancer cells. However, the development of effective therapeutic agents for brain cancer is insufficient. Brain cancer occurs regardless of age, and is characterized by having a higher frequency of occurrence in children than other cancers. Brain cancer collectively refers to primary brain cancer, which occurs in the brain tissue and the meninges surrounding the brain, and secondary brain cancer metastasized from cancers occurring in the skull or other parts of the body. Brain cancer is distinguished in many respects from cancers that occur in other organs. First, cancers occurring in the lungs, stomach, breasts, etc. are limited to one or two types for each organ, and their properties are the same or similar to each other, but many types of cancer occur in the brain. For example, these types of brain cancer include glioblastoma multiforme, malignant glioma, lymphadenoma, germ cell tumors, and metastatic tumors. In particular, glioblastoma multiforme (GBM), a type of glioma, is a very lethal disease which is the most malignant and aggressive type of brain tumor with a very poor prognosis and an average survival time of not more than 1 year after diagnosis. Since the boundary between brain cells and tumor cells in GBM is not clear, it is almost impossible to completely remove GBM by surgery. Thus, removal of GBM highly relies on treatment with anticancer drugs. However, most of anticancer drugs exhibiting effects in organs other than the brain have low efficacy in brain cancer because the transfer of the effects thereof to the brain is not smoothly achieved. Therefore, there is an urgent need to develop anticancer drugs exhibiting remarkable therapeutic effects specifically against brain cancer (N Engl J Med. 2005 Mar. 10; 352(10):987-96).

Meanwhile, gossypol as an aldehyde inhibitor is a phenol derivative that is contained in cotton plants in large amounts. In China, it was found that this gossypol inhibits male sperm function. Thus, gossypol has been developed for use as male oral contraceptives. However, it was recently published that gossypol has a significant effect on the inhibition of cancer cell growth (U.S. Pat. No. 6,114,397). However, it is still difficult to effectively inhibit cancer cell growth by administering gossypol alone.

Therefore, the present disclosure is directed to a pharmaceutical composition for treating brain cancer containing an aldehyde inhibitor and an anticancer drug. The pharmaceutical composition of the present disclosure may further contain a biguanide-based compound as needed, wherein the compound is preferably phenformin. The pharmaceutical composition according to the present disclosure is very effective for the treatment and improvement of prognosis of, particularly, brain cancer, and has remarkable effects of killing cancer cells and inhibiting cancer stem cell characteristics, compared to when each of the active ingredients is administered alone. Thus, it is expected that the pharmaceutical composition of the present disclosure will be widely used in the field of brain cancer treatment.

DISCLOSURE

Technical Problem

The present disclosure has been made in order to solve the above-described problems occurring in the prior art and is directed to a pharmaceutical composition for treating brain cancer containing an aldehyde inhibitor and an anticancer drug.

However, technical objects to be achieved by the present disclosure are not limited to the above-mentioned object, and other objects which are not mentioned herein will be clearly understood by those skilled in the art from the following description.

Technical Solution

Hereinafter, various embodiments described herein will be described with reference to the drawings. In the following description, numerous specific details, such as specific configurations, compositions, and processes, etc., are set forth in order to provide a thorough understanding of the present disclosure. However, certain embodiments may be practiced without one or more of these specific details, or in combination with other known methods and configurations. In other instances, known processes and preparation techniques have not been described in particular detail in order not to unnecessarily obscure the present disclosure. Reference throughout this specification to "one embodiment" or "an embodiment" means that a particular feature, configuration, composition, or characteristic described in connection with the embodiment is included in at least one embodiment of the present disclosure. Thus, the appearances of the phrase "in one embodiment" or "an embodiment" in various places throughout this specification do not necessarily refer to the same embodiment of the present disclosure. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present disclosure pertains.

In one embodiment of the present disclosure, "cancer" is characterized by uncontrolled cell growth, and refers to a state in which a cell mass called a tumor is formed by this abnormal cell growth, invades the surrounding tissue, and also metastasizes to other organs of the body in severe cases. Academically, it is also called neoplasia. Cancer is an intractable chronic disease that, even if treated with surgery, radiotherapy and chemotherapy, is not fundamentally cured in many cases, gives the patient pain, and ultimately leads to death. Cancer is caused by various factors which are divided into internal factors and external factors. Although a mechanism by which normal cells are transformed into cancer cells has not been clearly found, it is known that a significant number of cancers are caused by external factors such as environmental factors. The internal factors include genetic factors, immunological factors and the like, and the external factors include chemical substances, radiations, viruses and the like. Genes involved in the development of cancer include oncogenes and tumor suppressor genes, and cancer develops when a balance between these genes is broken by the above-described internal or external factors.

In one embodiment of the present disclosure, "cancer stem cells" generally refers to cancer cells having self-renewal or differentiation ability which is the characteristic ability of stem cells. For example, cancer stem cells may include a spherical cancer cell population or a cancer tissue having an unclear shape and poor prognosis. In the normal tumor growth conditions of cancer stem cells (the "normal tumor growth conditions" refers to a state in which a nutrient (glucose) necessary for cell growth is sufficient and conditions for tumor microenvironment growth are abundant, and thus there is no cell stress), the cancer stem cells may proliferate at a slow rate, unlike common cancer cells, or may be maintained in a dormant state, and thus may have resistance to anticancer drugs. For example, expression of transcription regulators such as PGC-1a may be controlled, unlike that in normal tumor cells, and thus the function of major metabolism regulatory substances therein may differ from that in common cancer cells. Thus, "cancer stem cells" generally refers to cells that acquire resistance to apoptosis in a nutrient-deficient state through this different metabolism regulatory ability and the regulation of cell signaling systems mechanistically linked thereto, and have invasive and/or metastatic potential. However, the cancer stem cells are not limited thereto and may include any cells that may differentiate into common cancer cells.

Anticancer drugs developed to date, which mostly target common cancer cells, are not effective in killing cancer stem cells that play an important role in treatment resistance and recurrence of cancer. When cancer stem cells remain in the body even after cancer treatment, the recurrence and/or metastasis of cancer actively occur(s). For this reason, it appears that the development of agents for treating cancer stem cells is an urgent task.

In one embodiment of the present disclosure, "treating cancer stem cells" is meant to include killing of cancer stem cells, inhibition of cancer stem cell maintenance, inhibition of cancer stem cell malignancy, and inhibition of cancer stem cell invasion.

In one embodiment of the present disclosure, "anticancer drug" refers to a collection of chemotherapeutic agents that are used for treatment of malignant tumors. Most anticancer drugs are agents that are involved in various metabolic pathways of cancer cells, thereby mainly inhibiting the synthesis of nucleic acids or exhibiting anticancer activity. Anticancer drugs that are currently used for cancer treatment are classified into 6 categories based on their biochemical mechanisms of action.

(1) Alkylating agents: The alkylating agents are very highly reactive substances having the ability to introduce an alkyl group (R—CH2) into any compound, and when acting on cells, they mostly react with N7 of guanine of DNA, deform the DNA structure, and cause chain cleavage, thereby exhibiting anticancer effects and cytotoxic effects. Examples of these drugs include ① nitrogen mustard-based drugs, including nitrogen mustard, chlorambucil, Melphalan, cyclophosphamide and the like; ② ethyleneimine-based drugs, including Thiotepa; ③ alkylsulfonate-based drugs, including busulfan; ④ triazine-based and hydrazine-based drugs, including DTIC (dacarbazine) and procarbazine; ⑤ nitrosourea-based drugs, including BCNU, CCNU, methyl-CCNU, etc.

(2) Metabolic antagonists (antimetabolites): Drugs belonging to this group act to inhibit metabolic processes required for cancer cell proliferation, and examples thereof include ① folic acid derivatives, including methotrexate (MTX); ② purine derivatives, including 6-mercaptopurine (6-MP) and 6-thioguinine; ③ pyrimidine derivatives, including 5-fluorouracil, cytarabine, etc.

(3) Antibiotics: Among antibiotics produced from bacteria, antibiotics exhibiting anticancer activity include adriamycin, daunorubicin, bleomycin, mitomycin-C, actinomycin-D, and the like.

(4) Mitotic inhibitors (vinca alkaloids): These drugs are division stage-specific drugs and stop cell division in the metaphase of mitosis. Examples thereof include vincristine, vinblastine, VP-16-213 and VM-26.

(5) Hormonal agents: Any kind of cancer can be effectively treated by administration of hormones. The use of male hormones is effective against breast cancer, the use of female hormones is effective against prostate cancer, and the use of progesterone is effective against endometrial cancer. Furthermore, adrenal cortex hormones are used for treatment of acute lymphocytic leukemia or lymphoma, and tamoxifen that is an anti-female hormonal agent is used for treatment of breast cancer.

(6) Others: Examples thereof include cisplatin, L-asparaginase, o,p-DDD and the like.

Despite continued efforts to develop effective anticancer drugs, current leading therapies are mainly surgery, radiation and chemotherapy. Chemotherapeutic approaches are mainly used for treatment of metastatic or particularly aggressive cancer.

Most of cancer chemotherapeutic agents that are currently used in clinical practice are cytotoxins. Cytotoxic agents work by damaging or killing cells that exhibit rapid growth. Ideal cytotoxic agents are required to have specificity to cancer and tumor cells without affecting normal cells. However, such ideal cytotoxic agents have not yet been found, and instead, agents that target especially rapidly dividing cells (both tumor and normal cells) have been used only. Accordingly, substances that are cytotoxic to cancer cells while exerting only mild effects on normal cells are highly desirable. Thus, there is a need to develop alternative anticancer drugs that can specifically inhibit the proliferation of tumor cells, and since the characteristics of the primary organs in which cancer occurs are different, there is a need to develop an organ-specific anticancer drug that reflects the characteristics of each tissue.

In one embodiment of the present disclosure, "metastasis" means that cancer cells spread from their primary organ to other organs, and "cancer", as used herein, is meant to include "cancer stem cells". The spread of cancer to other parts of the body is largely divided into one in which cancer tissue in primary cancer grows and directly invades the surrounding organs, and one in which cancer tissue metastasizes to other distant organs along blood vessels or lymphatic ducts. Metastasis can be controlled by inhibiting expression of cancer development-related genes or inhibiting the activities of the proteins encoded by the genes.

In one embodiment of the present disclosure, "gossypol" is a kind of aldehyde inhibitor compound contained in the separable pigmented lines of the seeds, leaves, stems and roots of some of plants belonging to the genus *Gossypium* of the family Malvaceae, and is also called polyphenolic gossypol or cottonseed pigment. It renders plants resistant to pests. It was reported that, when gossypol was added to poultry feed, the feed utilization and the egg productivity were reduced and the yolk decolorization of stored eggs occurred. On the other hand, ruminant livestock inactivates gossypol by fermentation. Free gossypol is physiologically toxic, whereas bound gossypol is inactive. The non-protein components of cottonseeds also bind to gossypol to form non-soluble and/or non-digestible complexes. This binding detoxifies gossypol in cottonseed meal, but reduces protein and biological values. When iron is added to free gossypol at a ratio of 2:1 or 3:1, it can effectively reduce the toxicity of gossypol in the liver. In China, it was found that this gossypol inhibits male sperm function. Thus, the gossypol has been studied for use as male oral contraceptives. In recent years, it has been reported that gossypol has a significant effect on the inhibition of cancer cell growth (U.S. Pat. No. 6,114,397). However, it is still difficult to effectively inhibit cancer cell growth by administering gossypol alone.

In one embodiment of the present disclosure, "biguanide-based compound" is preferably a biguanide-based antidiabetic agent, more preferably metformin, phenformin or buformine, even more preferably phenformin. However, the biguanide-based compound is not limited thereto and may be any biguanide-based compound that induces a nutrient deficiency-like state by inhibiting intracellular energy production.

In one embodiment of the present disclosure, "pharmaceutical composition" refers to a composition which is administered for particular purposes. With regard to the purpose of the present disclosure, the pharmaceutical composition of the present disclosure contains, as active ingredients, an aldehyde inhibitor and an anticancer drug, can effectively prevent and/or treat brain cancer, particularly glioblastoma, preferably by inhibiting the proliferation, maintenance, malignancy and invasion abilities of neurospheres, and may contain a compound which is involved therein and a pharmaceutically acceptable carrier, excipient or diluent. Furthermore, the pharmaceutical composition according to the present disclosure may further contain a biguanide-based compound, in addition to the above-described ingredients. The biguanide-based compound is preferably phenformin, and the anticancer drug is preferably temozolomide. In addition, the pharmaceutical composition according to the present disclosure contains the active ingredients of the present disclosure in an amount of 0.1 to 50 wt % based on the total weight of the composition. Examples of carriers, excipients and diluents, which may be contained in the composition of the present disclosure, include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil.

In one embodiment of the present disclosure, "treatment" or "treating" refers to a series of actions that are performed to alleviate and/or ameliorate the disease of interest. With regard to the purpose of the present disclosure, "treating" includes actions that inhibit an increase in the number or amount of cancer cells including cancer stem cells, or kill cancer cells, or inhibit the growth of cancer tissue, or reduce the size of cancer tissue, or inhibit the development of new blood vessels in cancer tissue.

In one embodiment of the present disclosure, "diagnosis" means confirming the presence or characteristics of a pathological condition. With regard to the purpose of the present disclosure, "diagnosis" means confirming whether cancer would develop, proliferate and metastasize, and "cancer" is meant to include "cancer stem cells". Cancer can be diagnosed by visual or cytological examination of a tissue from a patient suspected of developing cancer or having metastatic cancer. Specifically, cancer can be diagnosed by a method that uses an antibody specific to cancer contained in a tissue sample (clinically, cells, blood, fluid, pleural fluid, ascites, joint fluid, pus, secreted fluid, sputum, pharyngeal mucus, urine, bile juice, feces or the like) suspected of developing cancer or having metastatic cancer, or a method of directly detecting a cancer-related protein in the sample, or a method of directly detecting a nucleic acid encoding the cancer-related protein. Examples of diagnostic means that use antigen-antibody binding or a method of directly detecting the cancer-related protein include, but are not limited to, Western blotting, ELISA (enzyme linked immunosorbent assay), RIA (radioimmunoassay), radioimmunodiffusion, Ouchterlony immunodiffusion, rocket immunoelectrophoresis, immunohistological staining, immunoprecipitation assay, complement fixation assay, fluorescence activated cell sorter (FACS), protein chip assay, and the like. Examples of methods of directly detecting the nucleic acid encoding the cancer-related protein include, but are not limited to, reverse transcription-polymerase chain reaction (RT-PCR), competitive RT-PCR, real-time RT-PCR, RNase protection assay (RPA), Northern blotting, or DNA chip assay.

In one embodiment of the present disclosure, "administering" means introducing the composition of the present disclosure to a patient by any suitable method. The composition of the present disclosure may be administered by any general route, as long as it can reach a target tissue. Specifically, the composition of the present disclosure may be administered orally, intraperitoneally, intravenously, intramuscularly, subcutaneously, intradermally, intranasally, intrapulmonarily, intrarectally, intrathecally, intraperitoneally or intradurally, but the route of administration is not limited thereto. In the present disclosure, the effective amount may be adjusted according to various factors, including the kind of disease, the severity of the disease, the kinds and contents of active ingredient and other ingredients contained in the composition, the type of formulation, the patient's age, weight, general health condition, sex and diet, the time of administration, the route of administration, the secretion rate of the composition, the treatment period, and drugs that are concurrently used. For adults, the pharmaceutical composition for treatment may be administered in vivo in an amount of 50 ml to 500 ml for each time, the compound may be administered at a dose of 0.1 ng/kg to 10 mg/kg, and the monoclonal antibody may be administered at a dose of 0.1 ng/kg to 10 mg/kg. Regarding administration intervals, the composition may be administered 1 to 12 times a day. Where the composition is administered 12 times a day, it may be administered at 2-hour intervals. In addition, the pharmaceutical composition of the present disclosure may be administered alone or together with other therapies known in the art, for example, chemotherapeutic agents, radiotherapy and surgery, for treatment of the cancer stem cells of interest. Furthermore, the pharmaceutical composition of the present disclosure may be administered alone or in combination with other treatments designed to enhance immune responses, e.g., adjuvants or cytokines (or nucleic acids encoding cytokines) as well known in the art. Other standard delivery methods, such as biolistic transfer or ex vivo treatment, may also be used. In ex vivo treatment, antigen presenting cells (APCs) such as dendritic cells, peripheral blood mononuclear cells, or bone marrow cells, can be obtained from a patient or an appropriate donor and activated ex vivo with the pharmaceutical composition of the present disclosure, and then administered to the patient.

In one embodiment of the present disclosure, there is provided a pharmaceutical composition for treating brain cancer, the pharmaceutical composition containing an aldehyde inhibitor and an anticancer drug. In the pharmaceutical composition, the aldehyde inhibitor is any one or more selected from the group consisting of safrole, gossypol and coumarins. In the pharmaceutical composition, the anticancer drug is temozolomide. The pharmaceutical composition further contains a biguanide-based compound. In the pharmaceutical composition, the biguanide-based compound is any one or more selected from the group consisting of metformin, buformin and phenformin. In the pharmaceutical composition, the brain cancer is primary brain cancer or secondary brain cancer. In the pharmaceutical composition, the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis. In the pharmaceutical composition, the brain cancer includes brain cancer stem cells. In the pharmaceutical composition, the treating includes inhibiting an increase in the number of cancer cells, or inhibiting an increase in the amount of cancer cells, or killing cancer cells, or maintaining the size of cancer tissue, or decreasing the size of cancer tissue, or inhibiting the development of new blood vessels in cancer tissue.

In another embodiment of the present disclosure, there is a pharmaceutical composition for suppressing brain cancer metastasis, the pharmaceutical composition containing an aldehyde inhibitor and an anticancer drug. In the pharmaceutical composition, the aldehyde inhibitor is any one or more selected from the group consisting of safrole, gossypol and coumarins. In the pharmaceutical composition, the anticancer drug is temozolomide. The pharmaceutical composition further contains a biguanide-based compound. In the pharmaceutical composition, the biguanide-based compound is any one or more selected from the group consisting of metformin, buformin and phenformin. In the pharmaceutical composition, the brain cancer is primary brain cancer or secondary brain cancer. In the pharmaceutical composition, the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis. In the pharmaceutical composition, the brain cancer includes brain cancer stem cells.

Hereinafter, each step of the present disclosure will be described in detail.

Advantageous Effects

Since there are many types of brain cancer and the boundary between brain cells and tumor cells in brain cancer is not clear, brain cancer is particularly difficult to treat. The pharmaceutical composition for treating brain cancer according to the present disclosure, which contains an aldehyde inhibitor and an anticancer drug, may further contain a biguanide-based compound as needed, wherein the compound is preferably phenformin. The pharmaceutical composition of the present disclosure is very effective for the treatment and improvement of prognosis of brain cancer, and has remarkable effects of killing cancer cells and inhibiting cancer stem cell characteristics, compared to when each of the active ingredients is administered alone. Thus, it is expected that the pharmaceutical composition of the present disclosure will be widely used in the field of brain cancer treatment.

BEST MODE

Figure 1:
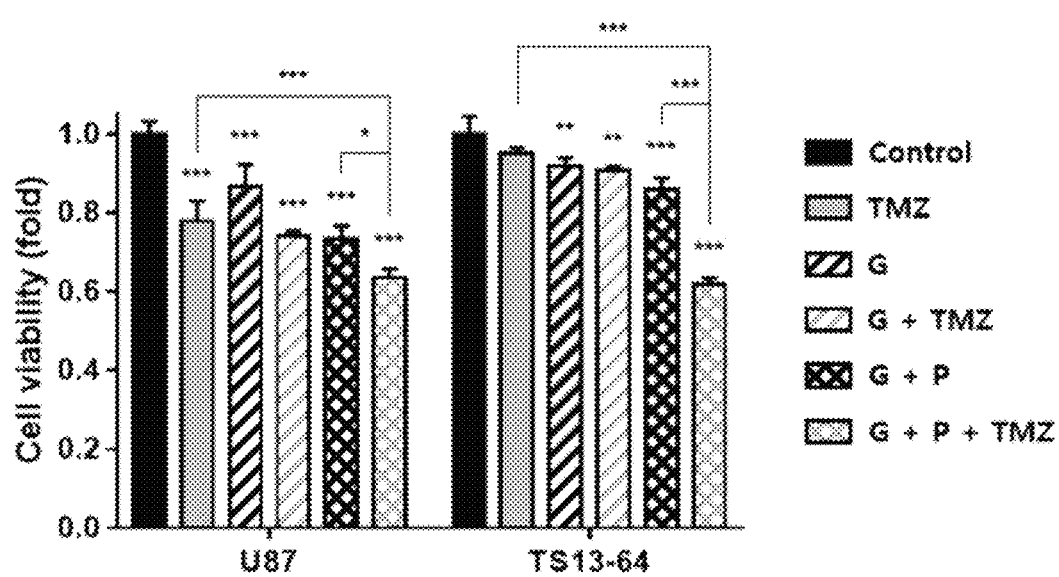
FIG. 1 shows the results of measuring cell viability after treating U87 and TS13-64 cells with gossypol, phenformin and TMZ alone or in combination according to an example of the present disclosure.

Cultured tumorsphere-forming glioblastoma cells (GBM TS) were seeded into 96-well plates at a density of $10^4$ cells/well and treated for 72 hours with a drug-containing medium prepared in a Preparation Example (a control group was treated with general culture medium), and then cytotoxicity to the cancer cells was measured by WST assay using EZ-Cytox reagent (DoGenBio, Seoul, Korea) according to the manufacturer's protocol. As a result of the experiment, it was confirmed that both spherical U87 cells and TS13-64 cells as cancer cells were more killed when treated with a combination of gossypol+TMZ than when treated with gossypol alone or TMZ alone. In addition, it was shown that the cancer cells were more killed when treated with a combination of gossypol+phenformin+TMZ than when treated with a combination of gossypol+TMZ or with a combination of gossypol+phenformin.

MODE FOR INVENTION

Hereinafter, the present disclosure will be described in more detail with reference to examples. It will be obvious to those skilled in the art that these examples serve merely to illustrate the present disclosure in more detail, and the scope of the present disclosure according to the subject matter of the present disclosure is not limited by these examples.

Preparation Example: Cell Culture and Reagents

For the present disclosure, two types of tumorsphere (TS)-forming glioblastoma (GBM) cells were used. TS13-64 cells are primary tumor cells derived from a GBM patient, and established from a new GBM tissue sample under the approval of the Institutional Review Board of the Yonsei University College of Medicine (approval Nos: 4-2012-0212 and 4-2014-0649). As U87 cells, spherical cells prepared by culturing the U87MG cell line under TS culture conditions were used. For TS culture, cells were treated with DMEM/F-12 medium containing 2 wt % 1×B27, 0.02 wt % bFGF (20 ng/ml), 0.02 wt % EGF (20 ng/ml) and 50 U/ml penicillin/50 mg/ml streptomycin (100×, Gibco, Invitrogen Korea, Seoul, South Korea), and all in vitro experiments were performed under TS culture conditions.

For use in in vitro experiments, gossypol (G) and phenformin (P, Sigma-Aldrich) were dissolved in DMSO and $H_2O$, respectively, at a concentration of 10 μM. The anticancer drug temozolomide (TMZ, Sigma-Aldrich) was dissolved in DMSO and used at a concentration of 250 μM. As controls for the anticancer drug TMZ for co-administration with gossypol and phenformin, other anticancer drugs, paclitaxel (PTX) and fluorouracil (5-FU), were used. Since the anticancer drugs have different toxicities and mechanisms, the concentration of each anticancer drug, which is clinically applied in the actual medical field, was reflected. That is, in the same manner as TMZ, paclitaxel was prepared and used at a low concentration of 2 nM and a high concentration of 5 nM, and fluorouracil was prepared and used at a low concentration of 50 μM and a high concentration of 100 μM (low concentration is indicated by L, and high concentration is indicated by H).

For in vivo experiments, gossypol was solubilized in DMSO and then mixed with the same volume of cremophor (Sigma-Aldrich), and phenformin was dissolved in PBS.

Example 1: Confirmation of Effect of Combination of Gossypol, Phenformin and TMZ Against Brain Cancer Cells Cultured tumorsphere-forming glioblastoma cells (GBM TS) were seeded into 96-well plates at a density of $10^4$ cells/well and treated for 72 hours with a drug-containing medium prepared in the Preparation Example (a control group was treated with general culture medium), and then cytotoxicity to the cancer cells was measured by WST assay using EZ-Cytox reagent (DoGenBio, Seoul, Korea) according to the manufacturer's protocol. As a result of the experiment, it was confirmed that both spherical U87 cells and TS13-64 cells as cancer cells were more killed when treated with a combination of gossypol+TMZ than when treated with gossypol alone or TMZ alone. In addition, it was shown that the cancer cells were more killed when treated with a combination of gossypol+phenformin+TMZ than when treated with a combination of gossypol+TMZ or with a combination of gossypol+phenformin. The results are shown in FIG. 1.

Figure 2:
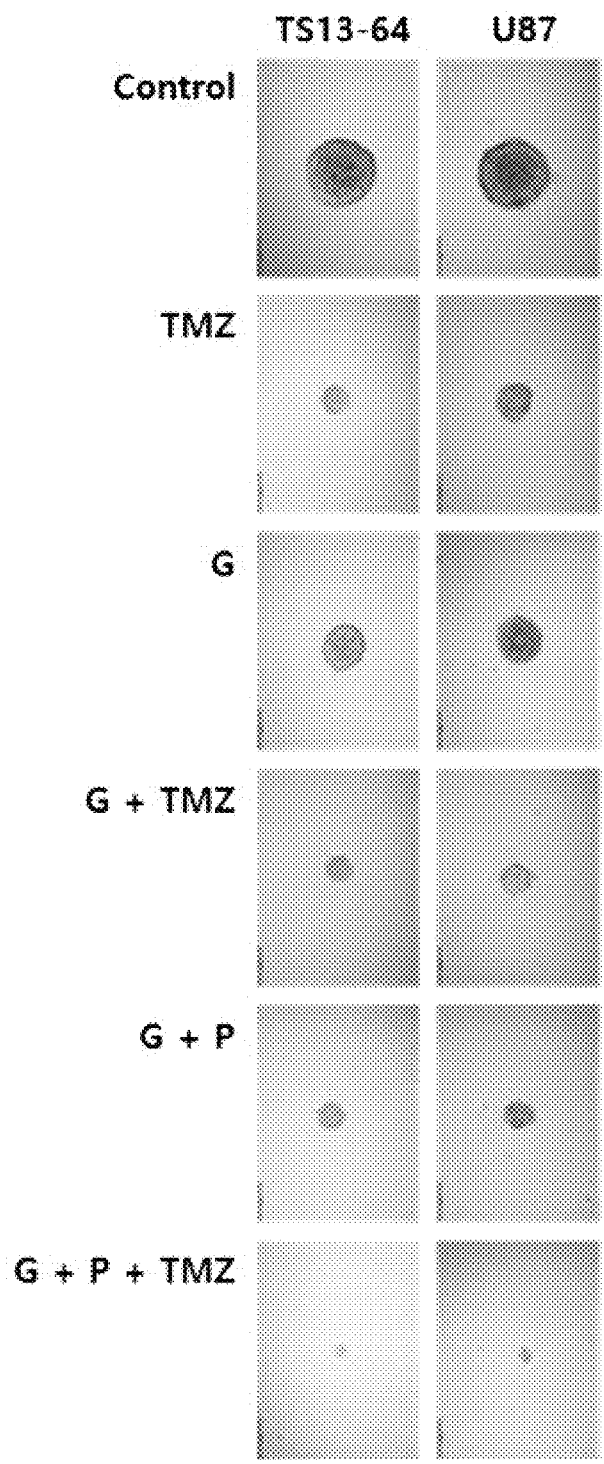
FIG. 2 depicts images showing the degrees of sphere formation of U87 and TS13-64 cells after treating the cells with gossypol, phenformin and TMZ alone or in combination according to an example of the present disclosure.
Figure 3:
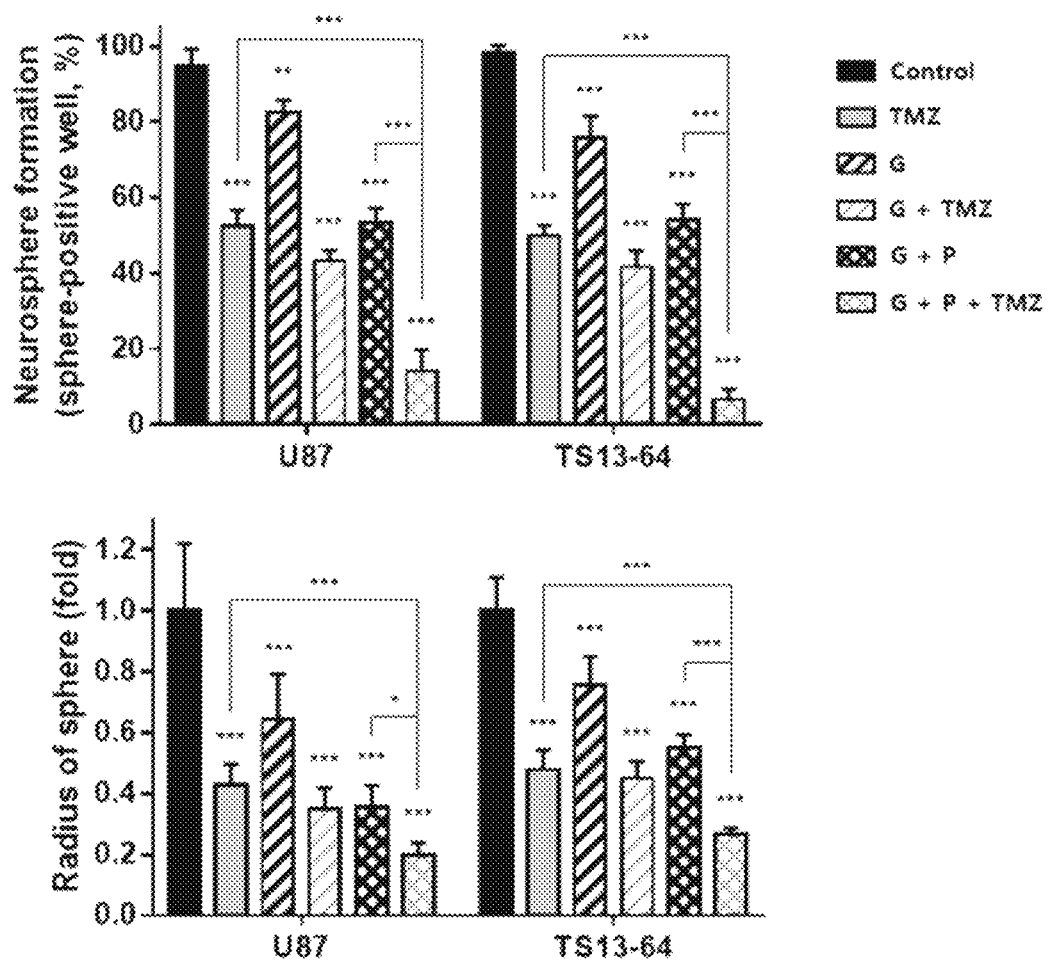
FIG. 3 shows the results of evaluating the sphere-forming abilities of U87 and TS13-64 cells after treating the cells with gossypol, phenformin and TMZ alone or in combination according to an example of the present disclosure.

Thereafter, the sphere-forming ability of cells depending on the kind of drug was evaluated. The sphere-forming ability is the ability of cancer stem cells to maintain their characteristics, and the effect of a drug on the treatment of cancer stem cells can be confirmed by evaluating the sphere-forming ability. To this end, 10 isolated single GBM TSs were first seeded into 96-well plates and cultured with TS culture medium for 3 weeks. The TS culture medium was replaced with fresh one every week. Thereafter, images were captured using ToupView software (ToupTek Photonics, Zhejiang, China), and the degrees of sphere formation and the sizes of the spheres were analyzed. The results of the analysis are shown in FIGS. 2 and 3. As a result of the experiment, like the results of the cytotoxicity experiment, it was confirmed that the effect of inhibiting the sphere-forming ability was better when treated with a combination of gossypol+TMZ than when treated with gossypol alone or TMZ alone, and that the effect of inhibiting the sphere-forming ability was better when treated with a combination of gossypol+phenformin+TMZ than when treated with a combination of gossypol+TMZ or a combination of gossypol+phenformin.

Figure 4:
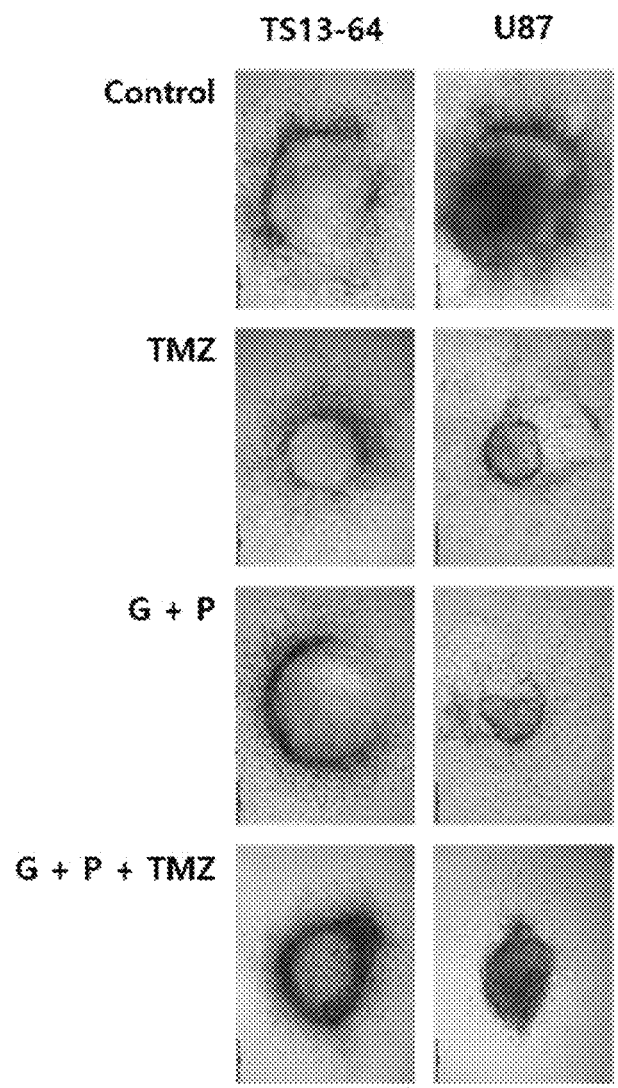
FIG. 4 depicts images showing the degree of invasion of U87 and TS13-64 cells after treating the cells with gossypol, phenformin and TMZ alone or in combination according to an example of the present disclosure.
Figure 5:
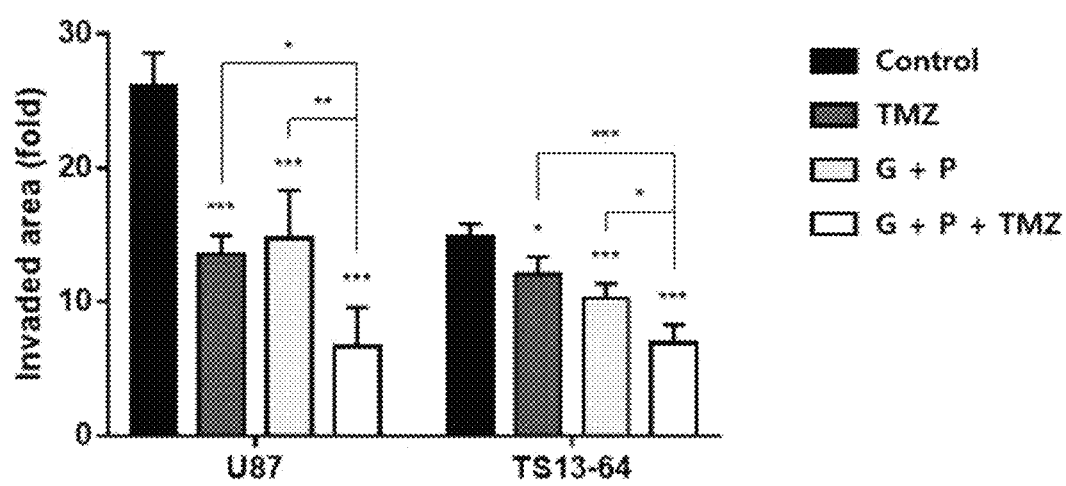
FIG. 5 shows the results of evaluating the invasion ability of U87 and TS13-64 cells after treating the cells with gossypol, phenformin and TMZ alone or in combination according to an example of the present disclosure.

Finally, the invasion ability of cancer cells was evaluated. Invasion is the most important factor for metastasis, and a factor that must be evaluated for metastasis inhibition, when considering that cancer growth and metastasis are different aspects. To this end, each well of 96-well plates was filled with a mixed matrix composed of Matrigel, collagen type I (Corning) and a TS culture medium containing a drug, and then seeded with GBM TS cells before gelation completely occurred. Thereafter, each corresponding TS culture medium was added onto the gelled matrix to prevent drying, and the invasion ability of the cells was evaluated by collagen-based 3D invasion assays. The images of the cells and the results of analyzing the invaded area are shown in FIGS. 4 and 5. The invaded area was quantified as occupied area at (72 h-0 h)/0 h. As a result of the experiment, it was shown that the invaded area greatly decreased when treated with TMZ compared to the control group to which only the TS culture medium was added, and that the invaded area significantly decreased when treated with a combination of gossypol+phenformin+TMZ compared to when treated with TMZ alone or with a combination of gossypol+phenformin.

Example 2: Confirmation of Effect of TMZ as Agent for Co-Administration with Gossypol and Phenformin An examination was made as to whether anticancer drugs other than TMZ also exhibit cancer therapeutic effects corresponding to TMZ when co-administered with gossypol and phenformin. Evaluation of cytotoxicity to cancer cells and the sphere-forming ability of cells was performed in the same manner as in Example 1.

Figure 6:
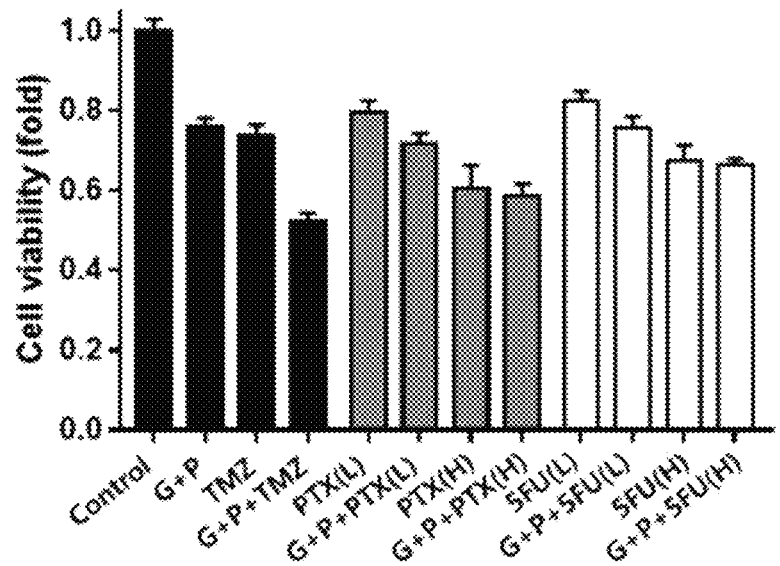
FIG. 6 shows the results of measuring cell viability after treating U87 and TS13-64 cells with the anticancer drug TMZ, PTX or 5-FU alone or in combination with gossypol+phenformin according to an example of the present disclosure.
Figure 6:
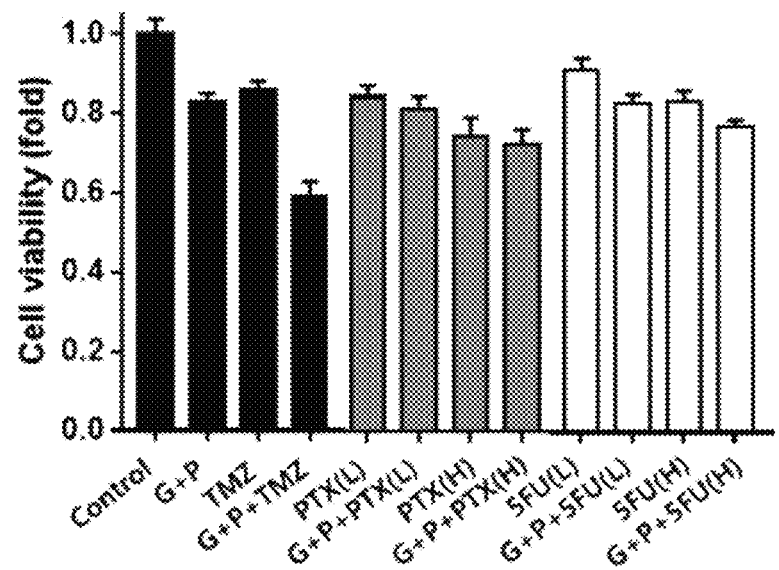
Figure 7:
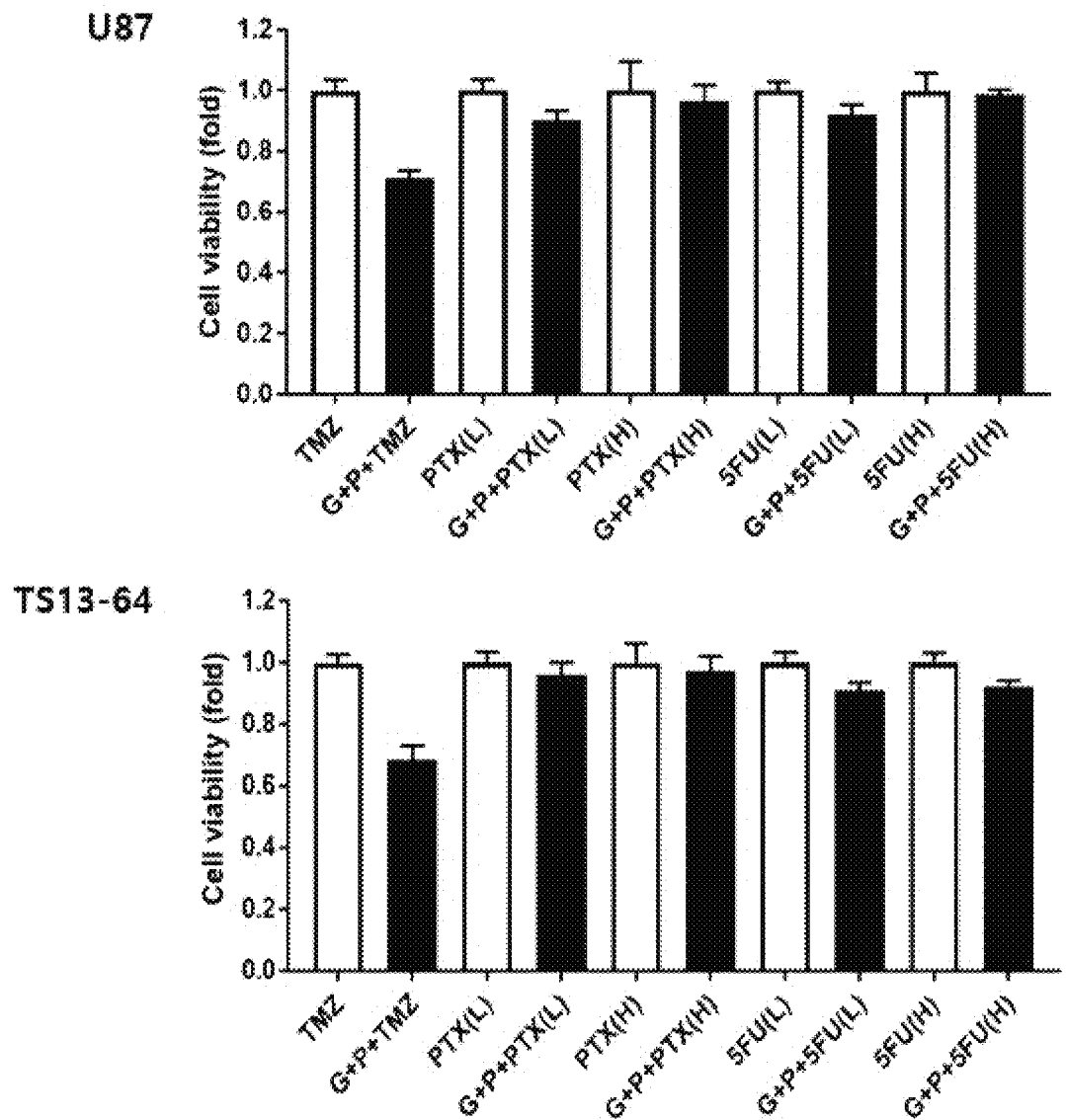
FIG. 7 shows the results of expressing the cell viability values, obtained after treating U87 and TS13-64 cells with the anticancer drug TMZ, PTX or 5-FU alone or in combination with gossypol+phenformin according to an example of the present disclosure, relative to the cell viability value obtained upon administration of each anticancer drug alone.

First, the results of evaluating cytotoxicity to cancer cells are shown in FIG. 6. The results of treating cancer cell the anticancer drug TMZ, PTX or 5-FU alone or in combination with gossypol+phenformin indicated that the synergistic effect of TMZ and gossypol+phenformin on cancer cell killing was significantly better than those of other anticancer drugs. Even in the case in which cancer cells were treated with a high concentration (H) of PTX or 5-FU, the cell-killing effect of administration of the anticancer drug PTX or 5-FU alone was higher than that of administration of TMZ alone, but the cell-killing effect of administration of the gossypol+phenformin combination was lower than that of co-administration of TMZ. In order to more easily compare these effects, the cell viability value obtained upon administration of each anticancer drug alone was set to 1, and the cell viability value obtained upon co-administration was expressed relative to the cell viability value obtained upon administration of each anticancer drug alone. The results are shown in Table 1 below and FIG. 7.

TABLE 1

| Cell | Drug administered | Measured value | Value expressed relative to administration alone | Effect of co-administration (cancer cell reduction rate) |
| --- | --- | --- | --- | --- |
| U87 | TMZ | 0.879 | 1.000 | 29.07% |
|  | G + P + TMZ | 0.624 | 0.709 |  |
|  | PTX(L) | 0.947 | 1.000 | 9.77% |
|  | G + P + PTX(L) | 0.855 | 0.902 |  |
|  | PTX(H) | 0.720 | 1.000 | 3.37% |
|  | G + P + PTX(H) | 0.696 | 0.967 |  |
|  | 5FU(L) | 0.980 | 1.000 | 8.09% |
|  | G + P + 5FU(L) | 0.901 | 0.919 |  |
|  | 5FU(H) | 0.804 | 1.000 | 1.34% |
|  | G + P + 5FU(H) | 0.793 | 0.986 |  |
| TS13-64 | TMZ | 0.781 | 1.000 | 31.40% |
|  | G + P + TMZ | 0.536 | 0.686 |  |
|  | PTX(L) | 0.764 | 1.000 | 3.87% |
|  | G + P + PTX(L) | 0.735 | 0.962 |  |
|  | PTX(H) | 0.675 | 1.000 | 2.70% |
|  | G + P + PTX(H) | 0.657 | 0.973 |  |
|  | 5FU(L) | 0.826 | 1.000 | 9.08% |
|  | G + P + 5FU(L) | 0.751 | 0.909 |  |
|  | 5FU(H) | 0.756 | 1.000 | 7.90% |
|  | G + P + 5FU(H) | 0.696 | 0.921 |  |

Figure 8:
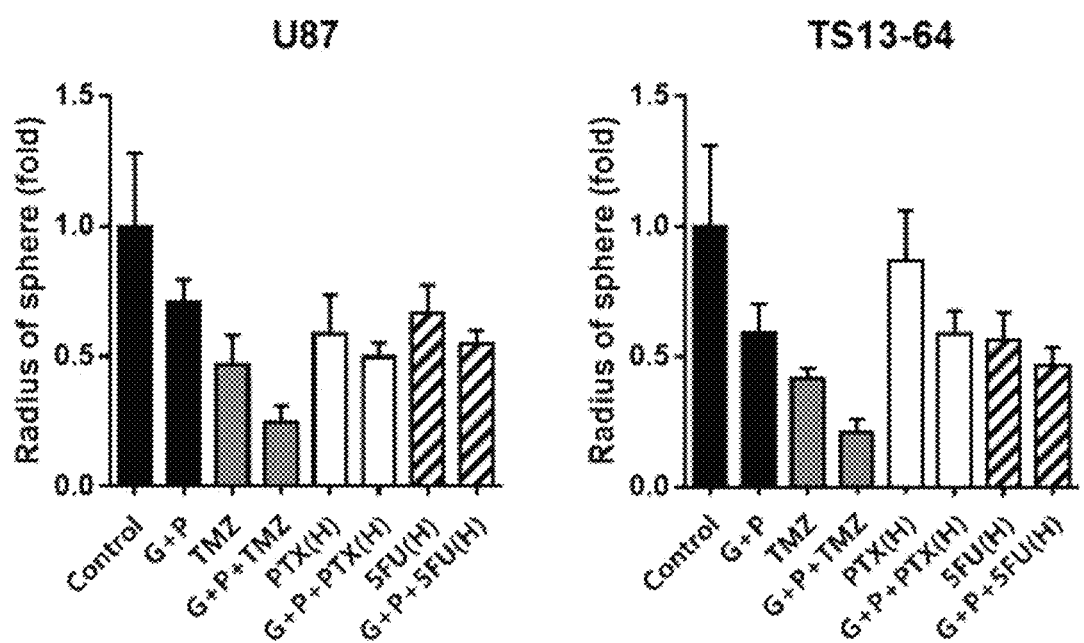
FIG. 8 shows the results of evaluating the sphere-forming abilities of U87 and TS13-64 cells after treating the cells with the anticancer drug TMZ, PTX or 5-FU alone or in combination with gossypol+phenformin according to an example of the present disclosure.

The effect of inhibiting the sphere-forming ability of the cancer cells was significantly better, particularly when TMZ was administered with gossypol+phenformin than when other anticancer drugs were administered. This is shown in FIG. 8.

In Examples 1 and 2 above, all data were processed by one-way analysis of variance using Tukey's post hoc test ($*P<0.05$, $P<0.01$, $*P<0.001$) and expressed as mean±SD.

Although the present disclosure has been described in detail with reference to the specific features, it will be apparent to those skilled in the art that this detailed description is only of a preferred embodiment thereof, and does not limit the scope of the present disclosure. Thus, the substantial scope of the present disclosure will be defined by the appended claims and equivalents thereto.

INDUSTRIAL APPLICABILITY

The pharmaceutical composition according to the present disclosure is very effective for the treatment and improvement of prognosis of, particularly, brain cancer, and exhibits remarkable effects of killing cancer cells and inhibiting the characteristics of cancer stem cells, compared to when each of the active ingredients is administered alone. Thus, it is expected that the pharmaceutical composition will be widely used in the field of brain cancer treatment.

The invention claimed is:

1. A method for preventing or treating brain cancer in a patient or for suppressing brain cancer metastasis in a patient, the method comprising administering to the patient a pharmaceutical composition comprising gossypol, phenformin and temozolomide as active ingredients.

2. The method of claim 1, wherein the method is for preventing or treating brain cancer in the patient.

3. The method of claim 2, wherein the brain cancer is primary brain cancer or secondary brain cancer.

4. The method of claim 3, wherein the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis.

5. The method of claim 2, wherein the brain cancer includes brain cancer stem cells.

6. The method of claim 2, wherein the treating includes inhibiting an increase in the number of cancer cells, or inhibiting an increase in the amount of cancer cells, or killing cancer cells, or maintaining the size of cancer tissue, or decreasing the size of cancer tissue, or inhibiting the development of new blood vessels in cancer tissue.

7. The method of claim 1, wherein the method is for suppressing brain cancer metastasis in the patient.

8. The method of claim 7, wherein the brain cancer is primary brain cancer or secondary brain cancer.

9. The method of claim 8, wherein the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis.

10. The method of claim 7, wherein the brain cancer includes brain cancer stem cells.

11. A method for preventing or treating brain cancer or for suppressing brain cancer metastasis in a patient, the method comprising administering to the patient gossypol, phenformin and temozolomide as active ingredients.

12. The method of claim 11, wherein the method is for preventing or treating brain cancer in the patient.

13. The method of claim 12, wherein the brain cancer is primary brain cancer or secondary brain cancer.

14. The method of claim 13, wherein the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis.

15. The method of claim 12, wherein the brain cancer includes brain cancer stem cells.

16. The method of claim 12, wherein the treating includes inhibiting an increase in the number of cancer cells, or inhibiting an increase in the amount of cancer cells, or killing cancer cells, or maintaining the size of cancer tissue, or decreasing the size of cancer tissue, or inhibiting the development of new blood vessels in cancer tissue.

17. The method of claim 11, wherein the method is for suppressing brain cancer metastasis in the patient.

18. The method of claim 17, wherein the brain cancer is primary brain cancer or secondary brain cancer.

19. The method of claim 18, wherein the brain cancer is any one or more selected from the group consisting of astrocytoma, glioblastoma, ependymoma, oligodendroglioma, mixed glioma, brain stem glioma, optic nerve glioma, pituitary adenoma, craniopharyngioma, medulloblastoma, primitive neuroectodermal tumors, pineal tumors, meningioma, schwannoma, metastatic brain tumors, CNS lymphoma, neurofibromatosis, pseudotumor cerebri, and tuberous sclerosis.

20. The method of claim 17, wherein the brain cancer includes brain cancer stem cells.

* * * * *